(12) United States Patent
Smith et al.

(10) Patent No.: US 7,754,480 B2
(45) Date of Patent: Jul. 13, 2010

(54) METHOD OF ISOLATING STEM CELLS

(75) Inventors: Clayton A. Smith, Tampa, FL (US);
Michael Colvin, Chapel Hill, NC (US);
Robert W. Storms, Durham, NC (US);
Susan M. Ludeman, Durham, NC (US)

(73) Assignee: Duke University, Durham, NC (US)

( * ) Notice: Subject to any disclaimer, the term of this patent is extended or adjusted under 35 U.S.C. 154(b) by 425 days.

(21) Appl. No.: 11/247,764

(22) Filed: Oct. 11, 2005

(65) Prior Publication Data
US 2006/0051833 A1 Mar. 9, 2006

Related U.S. Application Data

(60) Continuation of application No. 10/632,377, filed on Aug. 1, 2003, now Pat. No. 6,991,897, which is a division of application No. 09/701,413, filed as application No. PCT/US99/28769 on Dec. 7, 1999, now Pat. No. 6,627,759.

(60) Provisional application No. 60/111,195, filed on Dec. 7, 1998.

(51) Int. Cl.
*C12N 5/071* (2010.01)
*C12N 5/078* (2010.01)
*C12N 5/0789* (2010.01)

(52) U.S. Cl. ............................ 435/372; 366/29; 366/26

(58) Field of Classification Search .................. 435/372, 435/366
See application file for complete search history.

(56) References Cited

U.S. PATENT DOCUMENTS

| 4,774,339 | A | 9/1988 | Haugland et al. |
| 5,244,636 | A | 9/1993 | Walt et al. |
| 5,451,663 | A | 9/1995 | Kang et al. |
| 5,643,741 | A | * | 7/1997 | Tsukamoto et al. ........ 435/7.24 |
| 5,876,956 | A | 3/1999 | Jones et al. |

FOREIGN PATENT DOCUMENTS

WO    WO 96/36344    11/1996

OTHER PUBLICATIONS

Gai et al. "Chemoresistance in Breast Tumors," *Eur. J. Gynaecol. Oncol.*, 1991, pp. 359-374, vol. 12(5).
Jones, et al., "Assessment of Aldehyde Hydrogenase in Viable Cells," *Blood*, 1995, pp. 2742-2746. vol. 86(1).
Jones, et al., "Characterization of Mouse Lymphohematopoietic Stem Cells Lacking Spleen Colony-Forming Activity," *Blood*, 1996, pp. 487-491, vol. 88(2).
Kaiser, et al., "Determination of the Depth of BODIPY Probes in Model Membranes by Parallax Analysis of Fluorecence quenching," *Biochimica et Biophysica Acta*, 1998, pp. 13-22, vol. 1375.
Lindhal, "Aldehyde Hydrogenase in 2-Acetamidofluorene-Induced Rat Hepatomas," *Biochemical Journal*, 1977, pp. 119-123, vol. 164(1).
Storms, et al., "Aldehyde Dehydrogenase Activity as a Selectable Phenotype for Hematopoietic Progenitgors," *Blood*, 1998, Suppl. 1 Part 1-2,:59A, vol. 92(10).
Heithier, et al., *Biochemistry*, 1994, pp. 9126-9134, vol. 33.
Storms, R. W., et al., "Isolation of Primitive Human Hematopoietic Progenitors on the Basis of Aldehyde Dehydrogenase Activity," *Proc. Natl. Acad. Sci.*, Aug. 3, 1999, pp. 9118-9123, vol. 96, No. 16.
Goodell et al. (1996) "Isolation and Functional Properties of Murine Hematopoietic Stem Cells that are Replicating In Vivo" *J. Exp. Med.* 183:1797-1806.

* cited by examiner

*Primary Examiner*—Vera Afremova
(74) *Attorney, Agent, or Firm*—Alston & Bird LLP

(57) ABSTRACT

The present invention relates, in general, to stem cells, and in particular, to a method of isolating stem cells and to reagents suitable for use in such a method. The invention further relates to stem cell populations isolatable in accordance with the present method.

7 Claims, 6 Drawing Sheets

Figure 1A:
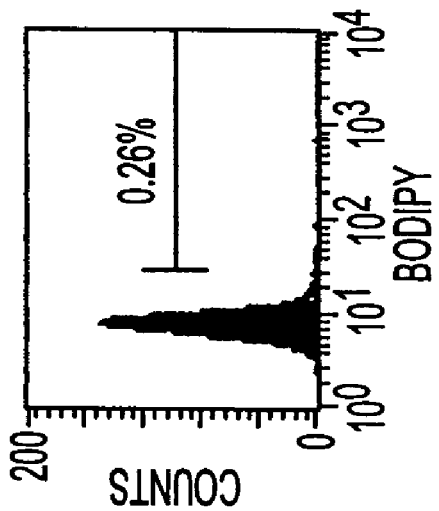

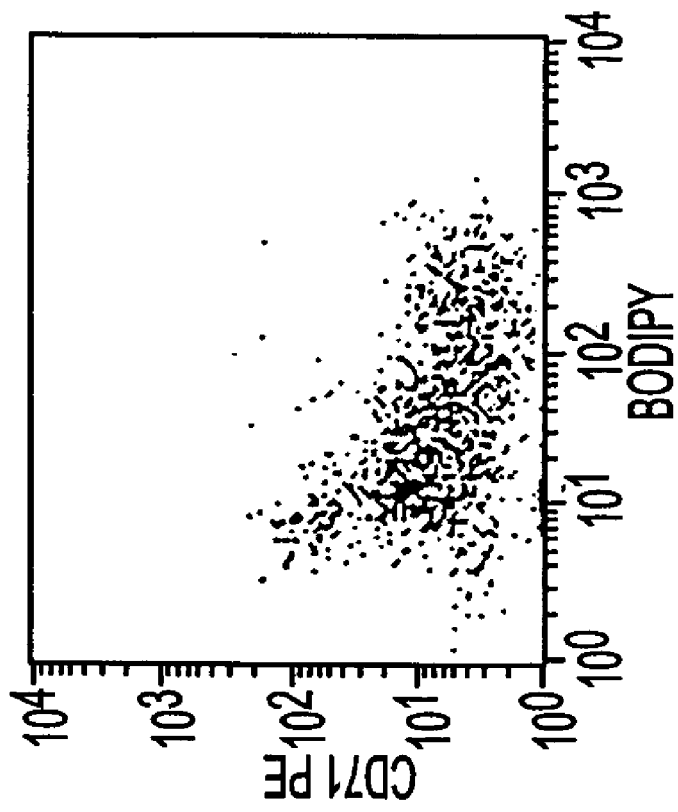
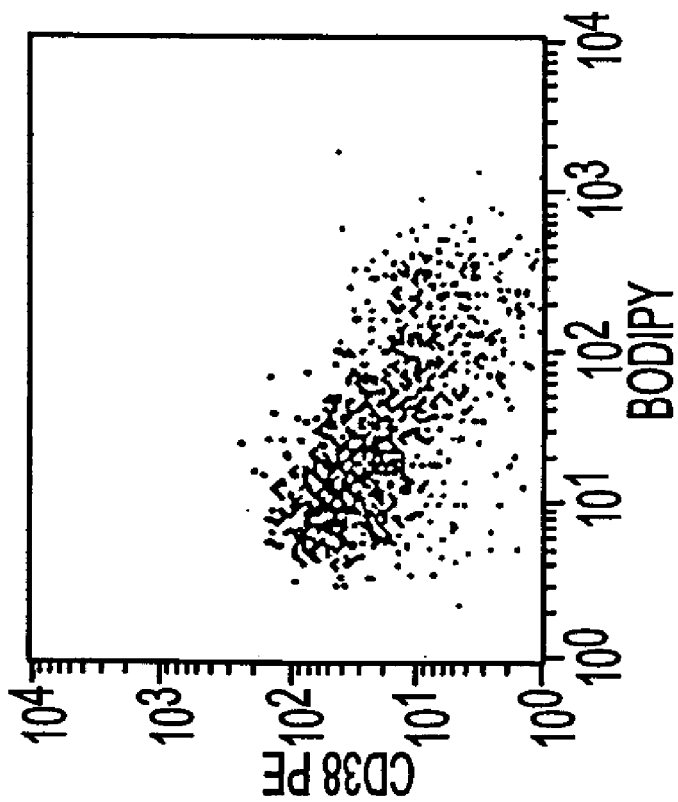

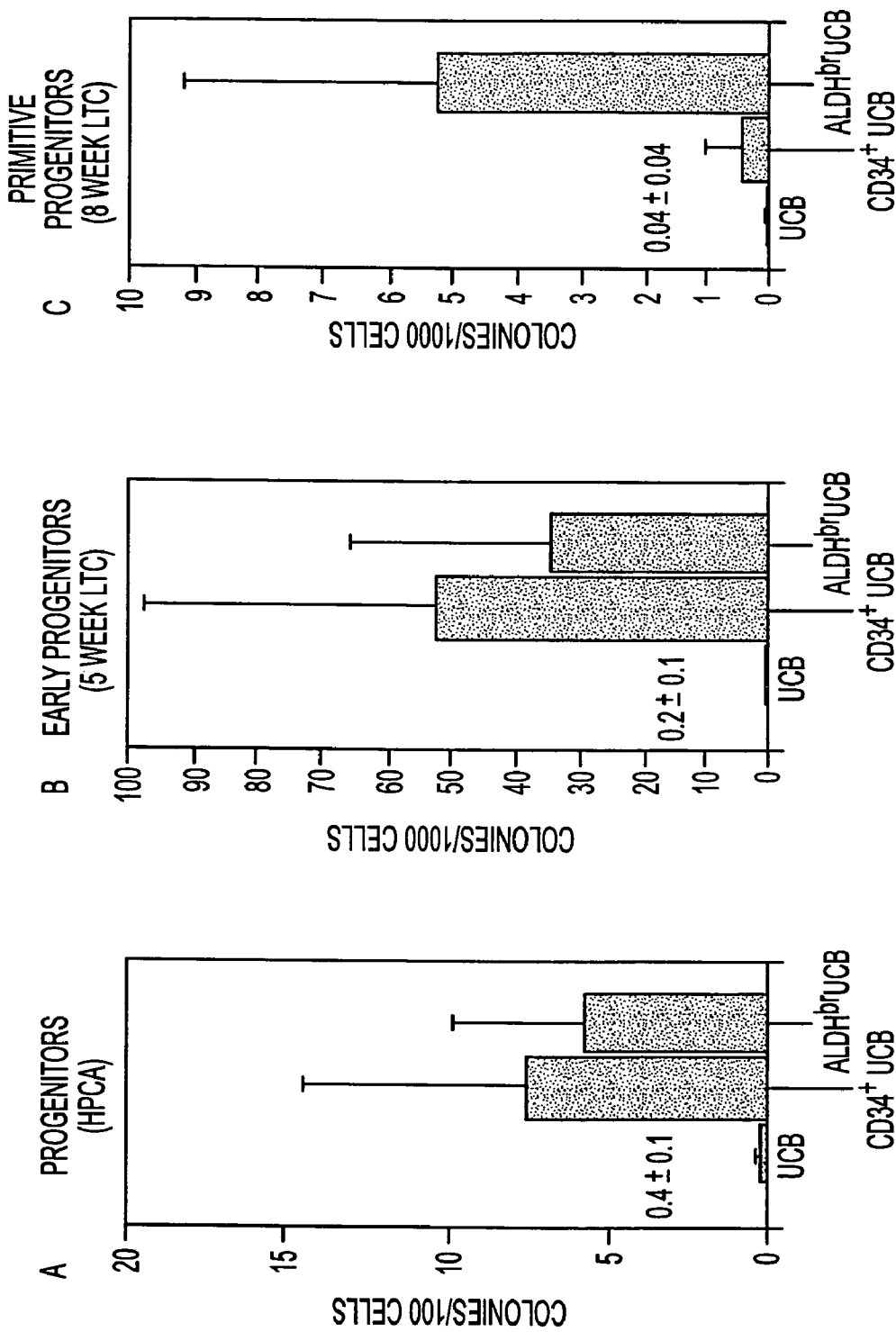

METHOD OF ISOLATING STEM CELLS

CROSS-REFERENCE TO RELATED APPLICATIONS

This application is a continuation of U.S. application Ser. No. 10/632,377, filed Aug. 1, 2003, which is a divisional of U.S. application Ser. No. 09/701,413, filed Feb. 20, 2001, which claims priority to the National Phase Entry of PCT/US99/28769, filed Dec. 7, 1999, which claims the benefit of U.S. Provisional Application No. 60/111,195, filed Dec. 7, 1998, all of which are hereby incorporated herein in their entirety by reference.

FEDERALLY SPONSORED RESEARCH OR DEVELOPMENT

The research underlying this invention was supported in part with funds from the National Institutes of Health grant no. CA16783. The United States Government may have an interest in the subject matter of this invention.

TECHNICAL FIELD

The present invention relates, in general, to stem cells, and in particular to a method of isolating stem cells and to reagents suitable for use in such a method. The invention further relates to stem cell populations isolatable in accordance with the present method.

BACKGROUND OF THE INVENTION

The most primitive hematopoietic stem cells (HSC) will reconstitute all of the hematopoietic lineages for an entire lifespan. These pluripotent hematopoietic stem cells (PHSC) are the transplantable cells that are ultimately the targets for gene delivery in stem cell-based gene therapies. One defining characteristic for PHSC is that they will survive most cytoablative conditioning regimens. The mechanisms for their resistance to these toxic agents suggest potential strategies by which these cells can be selected in vitro. One mechanism for drug resistance lies in the ability to efflux toxic substances out of the cell via the multiple drug resistance (MDR) pump. Fluorescent substrates for the MDR pump have permitted the isolation of PHSC based on their high capacity for dye efflux in a variety of assay systems. Drug resistances may also be conferred by more specific mechanisms. For example, a cytosolic aldehyde dehydrogenase (ALDH) mediates resistance to cyclophosphamide (CPA), an alkylating agent used in cytoreductive regimens in preparation for bone marrow transplant. Thus, expression of ALDH can be considered a selectable marker for true PHSC.

The therapeutic effectiveness of CPA has been attributed largely to the ability of PHSC and intestinal crypt cells to survive the drug regimen. Human hematopoietic progenitors express a cytosolic ALDH and primitive human HSC derived from mobilized peripheral blood stem cells can be selected when placed in culture with cyclophosphamide for 7 days. Jones et al. have demonstrated that long-term reconstituting murine PHSC can be isolated by providing a membrane-permeable fluorescent substrate for ALDH and by then selecting cells with the highest levels of ALDH activity (Jones (1995) *Blood* 85:2742; Jones et al. (1996) *Blood* 88:487). In these studies, dansyl aminoacetaldyde (DAAA) was used to stain murine bone marrow cells prepared by countercurrent elutriation.

Preliminary studies using DAAA indicate that this reagent is unusable on preparations of human hematopoietic cells because the signal intensity of the reagent is too high to resolve discrete cell populations by flow cytometry. The present invention provides a fluorescent ALDH substrate that is free of the problems associated with DAAA and that can be used in the purification of primitive human hematopoietic cells.

BRIEF SUMMARY OF THE INVENTION

The present invention relates to a novel reagent and method for isolating stem cells, including human stem cells. The reagent is a fluorescent substrate for ALDH. The method comprises staining a cell population that includes primitive stem cells with the substrate in the presence of an inhibitor of MDR activity. ALDH present in the cells converts the substrate to a product that is trapped within the cells. Since primitive stem cells have higher levels of ALDH activity than other cell types, these cells stain brighter than other cell types. The presence of the MDR inhibitor reduces the efflux of the converted substrate from the stem cells.

Objects and advantages of the present invention will be clear from the description that follows.

BRIEF DESCRIPTION OF THE SEVERAL VIEWS OF THE DRAWING(S)

Figure 1B:
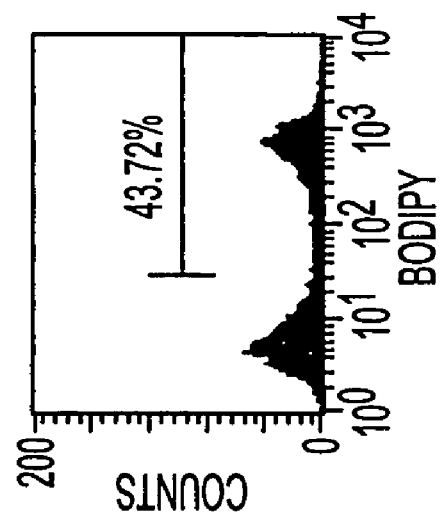
Figure 1C:
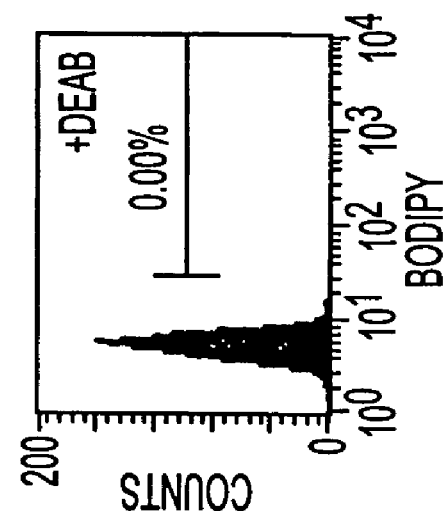
Figure 1D:
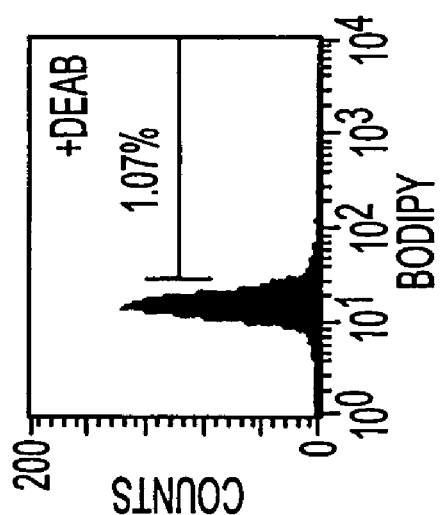

Having thus described the invention in general terms, reference will now be made to the accompanying drawings, which are not necessarily drawn to scale, and wherein:

FIGS. 1A-1D. BAAA staining identifies cells with high levels of ALDH activity. L1210/cpa is a derivative of the L1210 leukemic cell line that overexpresses ALDH. (FIGS. 1A and 1B represent L1210 cells, plus DEAB and minus DEAB, respectively; FIGS. 1C and 1D represent L1210/cpa cells, plus and minus DEAB, respectively).

Figure 2A:
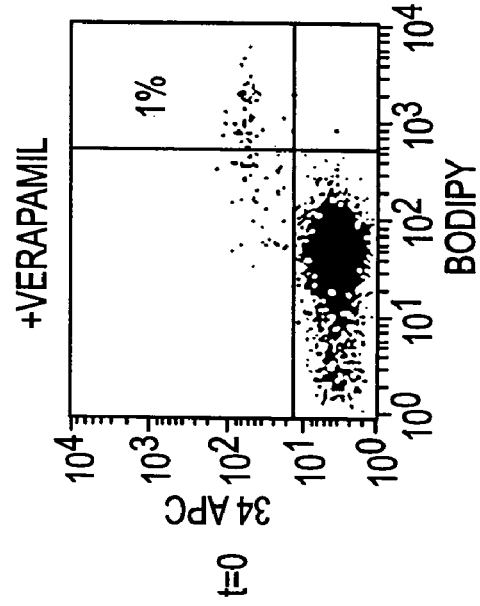
Figure 2B:
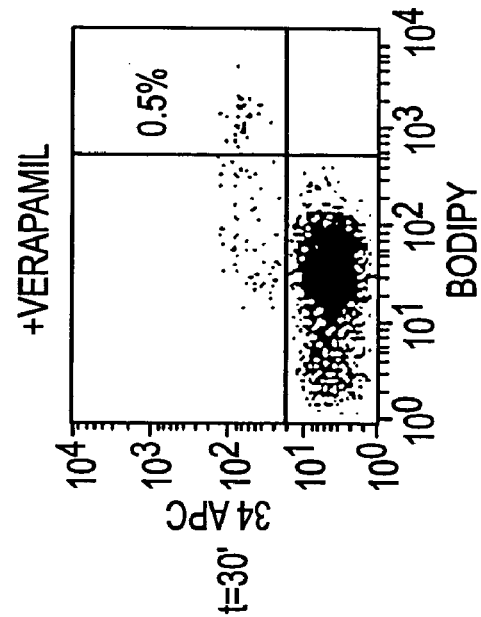
Figure 2C:
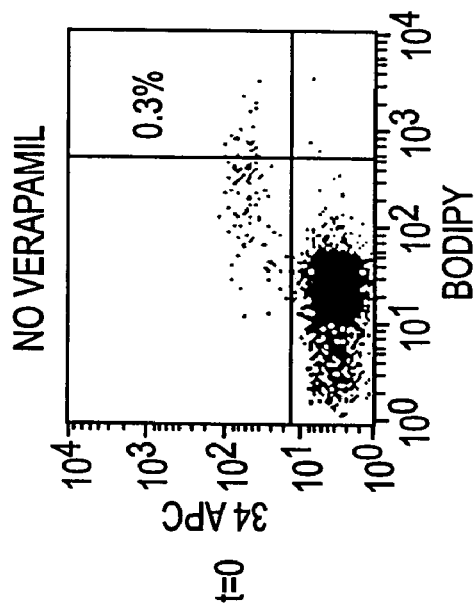
Figure 2D:
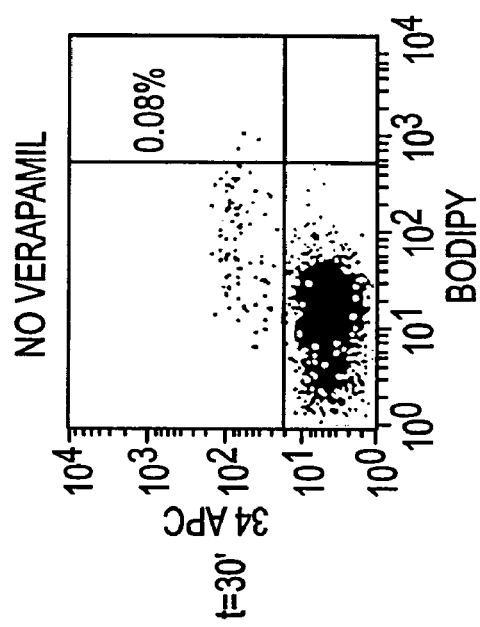

FIGS. 2A-2D. Converted BAAA is effluxed by an MDR pump from hematopoietic cells, particularly primitive CD34+ cells, as evidenced by the difference between the CD34+ cells that are BODIPY$^{bright}$ (FIG. 2B) in the presence and absence of the MDR inhibitor, verapamil (FIGS. 2A and 2B are at t=0, minus and plus verapamil, respectively; FIGS. 2C and 2D are at t=30', minus and plus verapamil, respectively.)

FIGS. 3A-3D. ALDH$^{br}$ cells (i.e., cells with low SSC properties that stain brightly with BAAA in the presence of an MDR inhibitor) are enriched for cells with the primitive CD34$^+$CD38$^{lo/-}$ immunophenotype traditionally associated with primitive stem cells.

FIGS. 4A and 4B. The staining intensity with BAAA correlates inversely with CD38 (FIG. 4A) and CD71 (FIG. 4B) expression in CD34$^+$ cells.

FIGS. 5A-5C. ALDH$^{br}$ cells are enriched for early progenitors equivalent to CD34$^+$ cells and are more enriched for very primitive progenitors than CD34$^+$ cells. (FIG. 5A=progenitors (HPCA), FIG. 5B=early progenitors (5 week LTC) and FIG. 5C=primitive progenitors (8 week LTC)).

Figure 6:
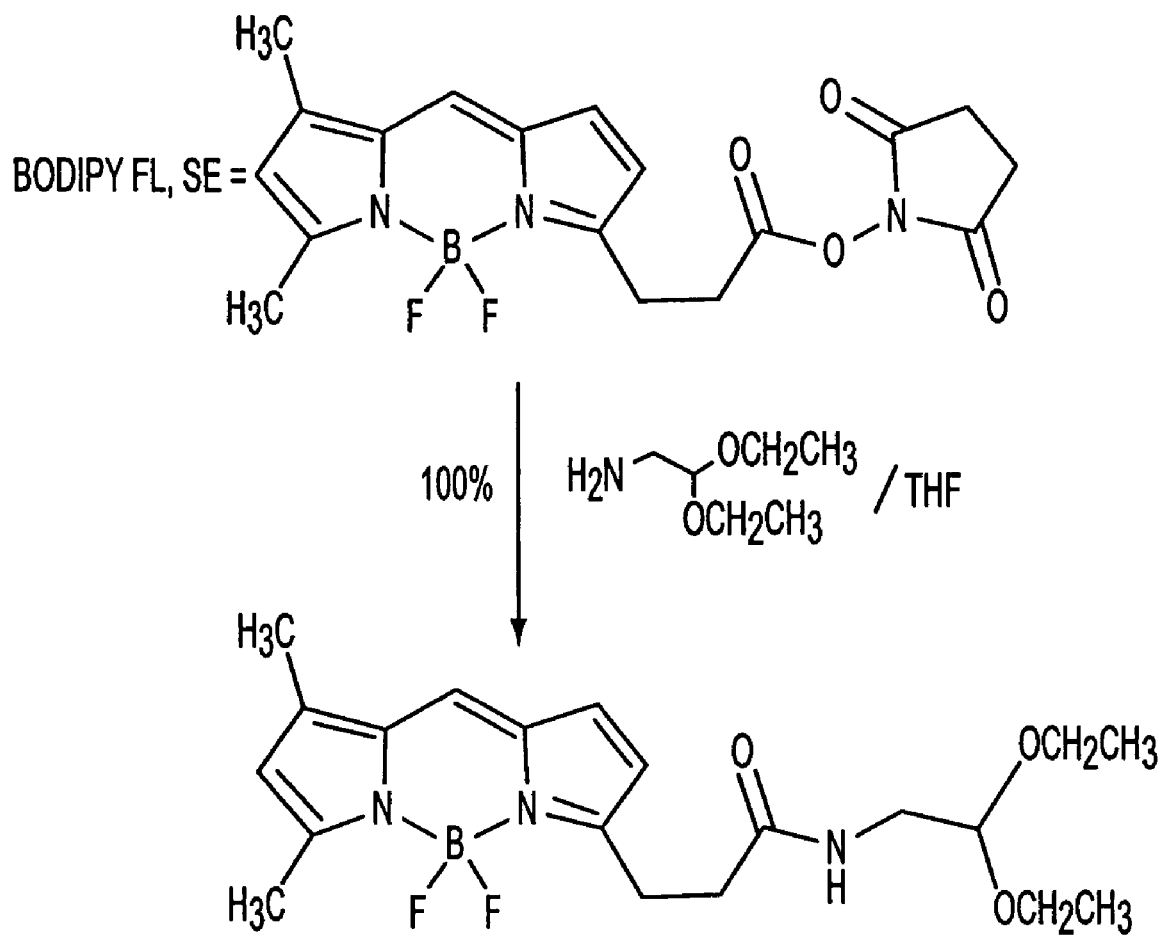

FIG. 6. Preparation of BODIPY-aminoacetaldehyde diethylacetal. Using an amber vial, a solution of aminoacetaldehyde diethyl acetal (0.019 mmol, Aldrich Chemical Co.) in dry tetrahydrofuran (THF, 0.5 mL) was added dropwise to a solution of BODIPY FL, SE (0.013 mmol, Molecular Probes) in dry THF (0.5 mL). Upon complete addition, the vial was capped and the reaction mixture was stirred for 30 min. The THF was evaporated and the residue was dissolved in minimal methylene chloride and then chromatographed on silica gel using ethyl acetate—hexane (1:1) as eluent. The product, BODIPY-aminoacetaldehyde diethylacetal was recovered in quantitative yield and identified by proton NMR.

DETAILED DESCRIPTION OF THE INVENTION

The present invention relates to a method of isolating stem cells and to a reagent suitable for use in such a method. The method comprises contacting a population of cells comprising stem cells with a detectable substrate for aldehyde dehydrogenase (ALDH), which substrate is converted to a detectable product by ALDH, that product being retained in the cells. In a preferred embodiment, the substrate is BODIPY-aminoacetaldehyde (BAAA) and efflux of converted BAAA from the cells, particularly the stem cells present in the population, is inhibited by the concurrent use of a MDR-inhibitor.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

Sources of cell populations that are suitable for use in the present invention include umbilical cord blood, bone marrow, peripheral blood and fetal liver. Any cell population that includes stem cells can be used regardless of tissue origin (e.g., gut, skin muscle, nerve, etc.). While the present method can be expected to be applicable to a variety of non-human mammalian cell populations, it is particularly useful in isolating human stem cells from sources including those referenced above.

Substrates suitable for use in the present invention include substrates for ALDH, particularly specific substrates for ALDH, that are detectable or bear a detectable label and that are converted, by the action of ALDH to products that are detectable or bear the detectable label which products are retained in the cells, particularly the stem cells. In a preferred embodiment, the substrate is a fluorescent substrate that has a discrete fluorescence emission profile identical to FITC. An example of such a substrate is BAAA.

The optimum amount of substrate to be added to the cell population can readily be determined by one skilled in the art (see Example). In the case of BAAA, concentrations can vary, for example, concentrations of about 1 µM to 5 µM can be used.

A concentrated solution of the substrate can be added directly to medium comprising the cells to be stained or harvested cells can be suspended in a substrate-containing medium.

In order to inhibit efflux of the converted substrate of the invention from the cells, concurrent use of an inhibitor of MDR is preferred. Any of a variety of MDR inhibitors can be used, including verapamil. The inhibitor can be added to the cells simultaneously with the substrate or prior to the addition of the substrate. The optimum amount of MDR-inhibitor to be used can be readily determined (e.g., by monitoring loss of staining). In the case of verapamil, concentrations can vary, for example, a concentration of about 50 µM can be used.

After exposure of the cell population to the substrate (and the MDR inhibitor) (e.g., about 30 minutes after), those cells that contain higher concentrations of labeled product can be separated from those that contain lower concentrations. In the case of the use of a fluorescent label, fluorescence activated cell sorting techniques can be used. Stem cells can be purified from other cells of the starting population based on low orthogonal light scattering on a flow cytometer (identifies small cells, like lymphocytes) and/or brightness of fluorescence. As shown in the Example that follows, sorting the brightest 1% of cells yielded a nearly 40-fold enrichment for cells that initiate long term cultures. The cell preparations that were recovered were up to 65% $CD34^+$ cells, most of which were $CD38^{-/dim}$ $CD71^{-/dim}$. The invention includes within its scope cell preparations that are greater than 50% $CD34^+$ cells, preferably greater than 75% $CD34^+$ cells, more preferably greater than 90% $CD34^+$ cells.

The stem cells isolated in accordance with the present invention have application in a variety of therapies and diagnostic regimens. They are suitable for both transplantation and gene therapy purposes. For example, isolation of stem cells from bone marrow or peripheral blood of patients with cancer can provide for the separation of stem cells from cancer cells. In patients undergoing autologous transplantation, such separation can be used to reduce the chance that cancer cells are returned to the patient. Purified autologous stem cells can be ex vivo expanded to hasten neutrophil, erythroid, and platelet engraftment after autologous transplantation. Ex vivo expansion can be effected by growth in defined cytokines, on stromal layers, and/or in bioreactors (Emerson et al. (1996) *Blood* 87:3082). In addition, the incidence of graft failure can be reduced. This is beneficial for cancer patients undergoing autologous transplantation, for patients suffering from auto-immune disorders, and for patients undergoing gene therapy.

Gene therapy approaches involving the present cells involve, in one embodiment, isolation of autologous stem cells, exposure of the isolated cells to a gene delivery vector and re-infusion of the modified cells into the patient (Smith, J. Hemather. 1:155 (1992)). This approach can involve ex vivo culture or the use of vectors capable of transferring genes into non-dividing cells, thereby rendering ex vivo culture unnecessary. Gene therapy can be useful in treating, for example, congenital diseases, such as sickle cell anemia, in which case the mutant β-globin gene is replaced or supplemented with either the wild type globin gene or an anti-sickling globin gene. In the treatment of cancer, drug resistance genes can be introduced into the stem cells to confer resistance to cytotoxic drugs. This can reduce the incidence and severity of myelosupporession. For the treatment of infectious diseases, including HIV, anti-viral genes can be introduced into the stem cells so that they are rendered resistant to the virus (Gilboa and Smith, Trends in Genetics 10:139 (1994)).

Isolation of stem cells results in the elimination of T-cells that cause GvHD. This elimination can be expected to reduce the incidence and severity of GvHD in recipients of allogeneic transplants.

Purified allogeneic stem cells can be ex vivo expanded to hasten neutrophil, erythroid, and platelet engraftment after allogeneic transplantation. In addition, the incidence of graft failure can be reduced. This is likely to be particularly important for recipients of umbilical cord blood transplants, where small cell doses limit the success of transplantation.

Successful engraftment with stem cells can also be expected to induce tolerance.

Such would clearly enhance solid organ transplantation.

It will be appreciated that cells of the present invention can be used as sources of new genes (e.g., for cytokines and cytokine receptors), including genes important in growth and development.

In addition to their application in treatment and diagnosis strategies, the stem cells of the invention can be used in screening protocols to identify agents that can be used, for example, to promote differentiation or growth and/or engraftment of hematopoietic cells. In one such protocol, stem cells are contacted with a test compound suspected of inducing differentiation and the ability of the test compound to effect differentiation determined (using, for example, microscopic and flow cytometric examination). In another screening protocol, stem cells are contacted with a test compound suspected of inducing proliferation and/or engraftment and the ability of the test compound to effect proliferation and/or engraftment determined using in vitro long term colony assays or in vivo immunodeficient mice models (eg SCID NOD mice). (See Peault et al. (1993) *Leukemia* 7: s98-101).

In addition to the above, the substrate of the invention can be used to identify tumors that may be resistant to cyclophosphamide via up regulation of ALDH activity.

In accordance with this embodiment, cells of the tumor can be contacted with the detectable substrate, e.g., BAAA, and MDR inhibitor under conditions such that the substrate enters the cells and is converted therein to the detectable product. Cells that stain brightly (e.g., with BAAA) can be expected to be cyclophosphamide resistant.

The invention also relates to kits that can be used to prepare the cells of the invention. The kits can comprise reagents (e.g., ALDH substrate) that can be used to effect isolation of the stem cells. In a preferred embodiment, the kit includes BODIPY aminoacetaldehyde diethyl acetal disposed within a container means. The kit can also include, disposed within a container means, an MDR inhibitor, such as verapamil.

Certain aspects of the present invention are described in greater detail in the non-limiting Examples that follow.

EXPERIMENTAL

Example 1

Preparation of BODIPY amino acetaldehyde diethyl acetal

The aldehyde dehydrogenase substrate is prepared as BODIPY aminoacetaldehyde diethyl acetal and lyophilized in 0.5 micromole aliquots. These preparations are stable indefinitely when stored at −20° C. The acetal is then solubilized in DMSO to a final concentration of 5 mM. This solution has been found to be stable at 4° C. for up to 1 week. To convert the acetal to an acetaldehyde, aliquots of this solution are brought to a final concentration of 1 N HCl. Under these conditions the acetal has a half life of 15 minutes. After 2 hours in 1 N HCl, the vast majority of the BODIPY aminoacetaldehyde diethyl acetal has converted to BODIPY aminoacetaldehyde (BAAA), and is then diluted to 200-250 mM in Dulbecco's phosphate buffered saline (PBS). This stock is added directly to cells prepared in Iscove's Modified Dulbecco's Medium (IMDM) with 2% FCS at concentrations ranging from 1 to 5 µM.)(See also FIG. 6.).

Antibody Reagents.

Directly-conjugated fluorescent antibodies directed against CD2 (Leu5; FITC), CD3 (Leu4; PerCP), CD5 (Leu1; PE), CD7 (Leu9; FITC), CD10 (CALLA; FITC), CD11b (Leu15; PE), CD14 (Leu M3; PE), CD19 (Leu12; FITC), CD33 (LeuM9; PE), CD34 (HPCA2; FITC and PE), CD38 (Leu17; PE), CD56 (Leu19; PE) and HLA-DR (FITC) from Becton Dickinson Immunocytometry Systems (BDIS; San Jose, Calif.) were used. Anti-CD7 (3A1; PE) and anti-CD45 (KC56; PE) were purchased from Coulter Corporation (Hialeah, Fla.); anti-CD3 (UCHT1; PE), anti-CD16 (3G8; PE), anti-CD19 (J4.119; PE) as well as the pooled anti-CD34 antibodies (QBEnd10, Immu-133, Immu-134; PE) from Immunotech, Inc. (Westbrook, Me.); anti-CD3 (B-B 11; FITC) and CD38 (B-A6; FITC) from BioSource International (Camarillo, Calif.); anti-CD45RA (F8-11-13; PE) from Southern Biotechnology Associates, Inc. (Birmingham, Ala.); and anti-CDw90 (5E10; PE) from PharMingen, Inc. (San Diego, Calif.).

Cell Lines.

K562, L1210 and L1210/cpa cells (ATCC) were maintained in suspension in RPMI 1640 media supplemented with 10% Fetal Calf Serum (FCS) and $5 \times 10^{-5}$ M β-mercaptoethanol.

Preparation of Human Umbilical Cord Blood.

Human umbilical cord blood (UCB), intended for disposal, was collected into sterile bottles containing anticoagulant citrate buffer. The UCB used in these studies were processed within 24 hours of being harvested. White cells were enriched through a preliminary red cell agglutination where the UCB was diluted 1:2 with Dulbecco's phosphate buffered saline (PBS) at room temperature. These cells were then brought to a final concentration of 1% Hespan (DuPont Pharma, Wilmington, Del.) and were left to stand undisturbed for 1 hour. Non-agglutinated white blood cells were harvested and residual red cells were hemolysed at 37° C. in 0.17 M $NH_4Cl$ containing 10 mM Tris-HCl, pH 7.2 and 200 mM EDTA. The recovered cells were washed in IMDM containing 2% FCS and mononuclear cells are then purified using Ficoll-Hypaque (1.077 g/ml). When held overnight, the cells were kept on ice in a 4° C. refrigerated room in IMDM with 20% FCS.

Cell Staining and Fluorescence-Activated Cell Sorting.

Mononuclear UCB cells were resuspended at $10^6$ cells/ml in IMDM containing 2% FCS and were labeled with 1 µM BAAA for 30 min. When used, verapamil was included at 50 mM. After staining, the cells were washed with ice cold staining media and maintained on ice until their analysis and sorting. The cells were then resuspended in staining media with 10 mg/ml 7-aminoactinomycin D (7AAD) (Molecular Probes; Eugene, OR). For antibody staining to permit multi-parameter analyses, the cells were resuspended in staining media (100 µl) and antibodies were added directly to the cell suspensions. The cells were incubated on ice for 20 min. and then washed again in ice cold staining media. The cells were then analyzed or sorted on a FAC Star Plus cell sorter (BDIS) equipped with dual Coherent I -90 argon-dye laser. The BAAA was excited at 488 nm and emissions were detected using 515 DF20filter in FL1. Dead and dying cells were excluded on the basis of their high emission in the far red wavelength due to their uptake of 7AAD.

For analyses of cell surface antigens on cells previously sorted based on BAAA staining, the cells were pelleted and resuspended in IMDM with 2% FCS. The cells were then held at 37° C. for 1-2 hours to permit efflux. The cells were then pelleted and fluorescence-conjugated antibodies were added directly to the cells. Following incubations for 20 minutes, the cells were washed with PBS/2% FCS and were fixed in 1% formaldehyde in PBS/2% FCS. In all surface marker analyses, no differences were noted between analyses with cells stained simultaneously with BAAA and with antibodies and those analyses performed on FACS® sorted cells that were subsequently stained with antibodies.

Hematopoietic Progenitor Colony Assays and Long Term Cultures.

$ALDH^{br}$ cells were isolated directly from mononuclear UCB cells which had been stained with BAAA. For these assays, the $ALDH^{br}$ was defined as 1% of the lymphocyte gate of the UCB.

Hematopoietic progenitor colony assays were performed by plating 100-200 cells in MethoCult H4431 containing agar leukocyte conditioned media and recombinant human erythropoietin (StemCell Technologies, Inc.). The cells were incubated in a humidified chamber at 37° C. with 5% $CO_2$. Hematopoietic colonies (>100 cells) were then scored at 14 to 18 days after initiating the cultures. Long term cultures were maintained on stromal layers of murine MS-5 cells (provided by Dr. Tadashi Sudo of the Kirin Pharmaceutical Research Laboratory, Gunma, Japan) (Issaad, Blood 81:2916 (1993)). MS-5 stromal cells were seeded into 24-well plates (Coming Costar Corp., Cambridge, MA) at $5\times10^4$ cells/well in DMEM supplemented with 10% FCS and cultured at 37° C. When the monolayers approached 80% confluence they were γ-irradiated from a cesium source (40 Gy). After irradiation, fresh media was provided to the cultures. For the MS-5 cells, the culture media was replaced entirely with MEMα supplemented with 10% FCS, 10% equine serum, β-mercaptoethanol, pyruvate. Long term cultures were initiated with 400-2000 hematopoietic progenitor cells/well and were maintained at 33° C. with 5% $CO_2$. At weekly intervals half the media from each well was removed so that the media could be replenished. Adherent and non-adherent cells were harvested after 5 or 8 weeks and plated into HPC assays as described above. As shown in the Example that follows, sorting the brightest 1% of cells yields a nearly 40-fold enrichment for cells that initiate long term cultures. The cell preparations that were recovered were up to 65% $CD34^+$ cells, most of which were $CD34^+$ cells, most of which were $CD38^{-/dim}$ $CD71^{-/dim}$.

Results

Synthesis of BODIPY aminoacetaldehyde diethyl acetal.

Due to the inherent instability of aldehydes in aqueous solution, the reagent is prepared and stored as an acetal. Immediately prior to its use, the acetal is converted to an aldehyde in 1 N HCL. the aldehyde is freely soluble in PBS and can be added directly to cells prepared in IMDM with 2% fetal calf serum at $10^6$ cells per ml. As an aminoacetaldehyde, the reagent is membrane permeable; however, in the presence of the aldehyde dehydrogenase (ALDH), the aldehyde moiety is converted to a carboxylic acid that is retained in the cell. Intracellular fluorescence can be used to select cells.

Converted BAAA is a Specific Substrate for ALDH.

To assay whether BAAA would permit the specific selection of $ALDH^+$ cells, studies initially determined an optimal response dose for the BAAA reagent in a murine cell line previously selected for cylophoshamide-resistance, L1210/cpa, that is known to be $ALDH^+$ (FIG. 1). The parental cell line, L1210 (FIGS. 1A and 1B) is cylophosphamide-sensitive and $ALDH^-$. This cell line exhibited essentially no response to BAAA. In addition, a potent inhibitor of ALDH, diethylbenzaldehyde (DEAB), was used to demonstrate the specificity of the BAAA signal. A 10-fold molar excess of DEAB totally blocked the fluorescent response (FIG. 1C). Therefore, BAAA was able to detect $ALDH^+$ cells. In these studies, the BAAA could be used at a final concentration as low as 5 μM. This molar concentration is 10-fold lower than that used with the dansylated reagent.

Multiple different ALDH isoenzymes exist and these may display different abilities to convert BAAA. It has been suggested that resistance to cyclophosphamide is primarily mediated by a specific ALDH isoenzyme, ALDH1. Therefore, a human cell line known to express ALDH1, K562, was assayed with this novel reagent. K562 cells converted BAAA and were positive for ALDH in these assays. This response was entirely inhibited by DEAB. Thus, BAAA can serve as a specific substrate for human ALDH1 and can be used to identify primary human cells that demonstrate resistance to cyclophosphamide.

Primary UCB Cell Preparations Contain Subsets of $ALDH^{br}$ Cells.

Having demonstrated the effectiveness of this reagent on continuous cell lines, BAAA was assayed on primary human cells. Umbilical Cord Blood (UCB) was chosen for its increasing promise as a source for transplantable hematopoietic stem cells. For these studies, the UCB was unfractionated except for having been prepared for mononuclear cells over Ficoll-Hypaque. This separation is significant in that two mature $ALDH^+$ cell types, erythrocytes and megakaryocytes, are removed. The BAAA was tested on UCB cells prepared in IMDM with 2% FCS at $10^6$ cells/ml (FIG. 2). The UCB cells were very responsive to the BODIPY reagent, and appeared to be much more sensitive than the continuous cell lines had been. The BAAA was therefore titrated to an optimal concentration of 1 μM. This was the best concentration for resolving $ALDH^{br}$ subpopulations. The response was inhibited in the presence of excess DEAB and was therefore specific for ALDH. This molar concentration is 50-fold lower than the concentration of dansyl aminoacetaldehyde that had previously been used to detect murine pluripotent hematopoietic stem cells.

Figure 3A:
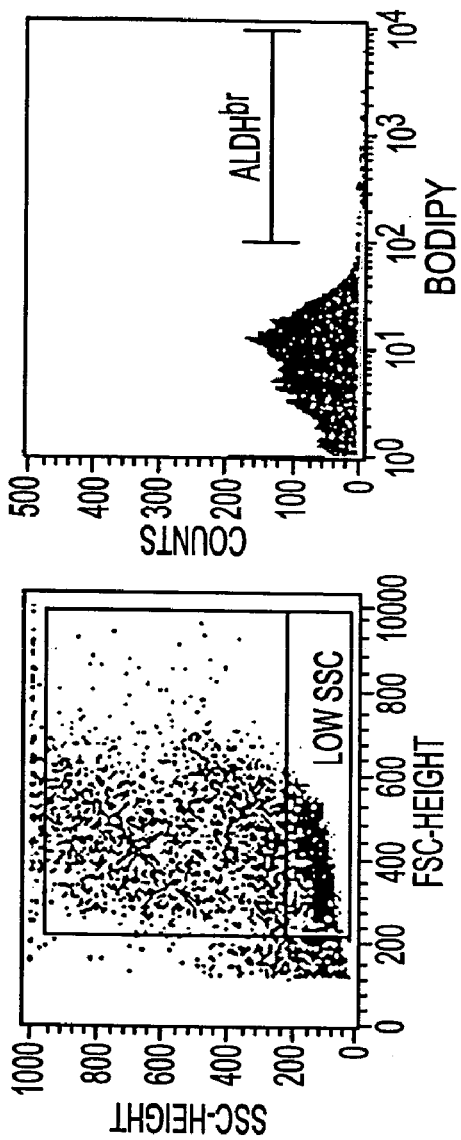
Figure 3B:
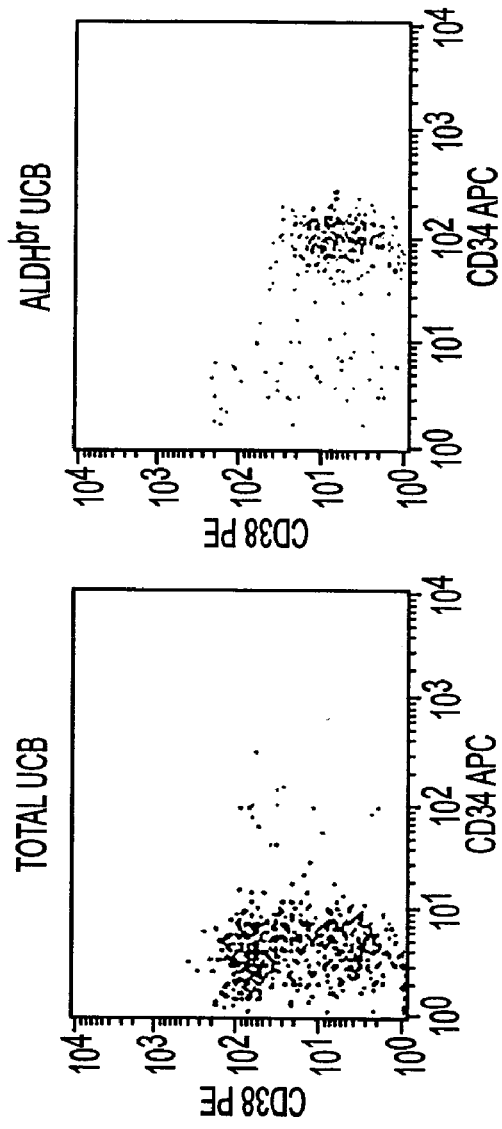
Figure 3C:
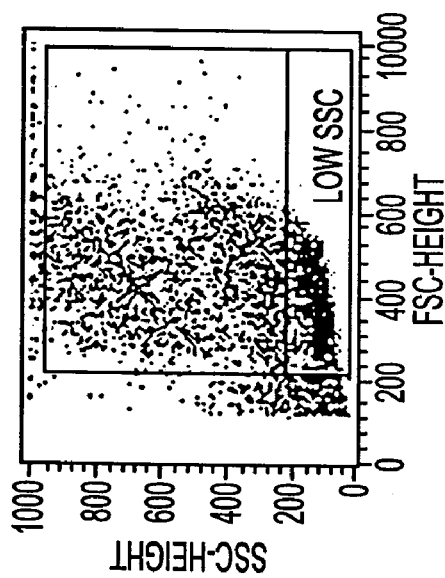

The fluorescence emission from BAAA-stained UCB cells exhibited a bimodal response. The brighter peak of fluorescence emission was attributed to mature monocytes, suggesting monocytes express a uniform level of ALDH. Hematopoietic stem cells are small, non-complex cells. Indeed, murine $ALDH^+$ PHSC were first enriched using countercurrent elutriation. Therefore, the BODIPY signal was examined only in non-complex cells that exhibited low inherent orthogonal light scattering ($SSC^{lo}$) (FIG. 3A). The majority of the $SSC^{lo}$ UCB cells were $ALDH^{neg/dim}$ (FIG. 1B). This was not unexpected since the $SSC^{lo}$ cells are predominantly lymphocytes, and most lymphocytes do not express ALDH. However, a small, clearly-defined subpopulation of the $SSC^{lo}$ UCB cells was $ALDH^{br}$ (FIG. 3A).

BODIPY Aminoacetate is a Substrate for the MDR Efflux Pump.

In addition to expressing ALDH, PHSC should also express high levels of the P-glycoprotein or multiple drug resistance (MDR) efflux pump. Since this reagent had never been previously characterized, the susceptibility of converted BAAA to MDR efflux was assayed. Although BODIPY aminoacetaldehyde passes through the cell membrane without active transport, the product of the ALDH conversion (BODIPY aminoacetate) might well be a substrate for the MDR pump. To investigate this possibility, UCB cells were stained with BAAA in the presence of 50 μM verapamil, a competitive inhibitor of the MDR efflux pump. The verapamil-treated cells exhibited a consistently-higher fluorescence when compared with BAAA-stained cells that had not been simultaneously treated with verapamil (FIG. 2). A substantial population of $ALDH^{dim}$ cells were effected by the verapamil treatment. Most importantly, the percentage of $ALDH^{br}$ cells increased by 1.8 fold in the presence of verapamil. In verapamil-treated cells, the $ALDH^{br}$ subpopulation was equivalent to 0.8±% of the $SSC^{lo}$ cells. In contrast, in cell preparations that received no verapamil, the same fluorescence intensity represented only 0.46±% of the $SSC^{lo}$ cells. This indicated that the $ALDH^{br}$ $SSC^{lo}$ UCB cells retain the converted BAAA more effectively if the efflux activity of the MDR pump is inhibited.

$ALDH^{br}$ $SSC^{lo}$ UCB Cells are Highly Enriched for Primitive $CD34^+$ Cells.

Figure 3D:
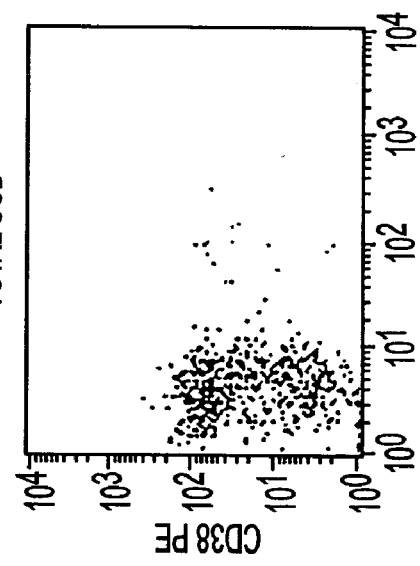

With verapamil treatment, the ALDH$^{br}$ SSC$^{lo}$ UCB cells contained almost 90% CD34$^+$ cells, indicating that at least some hematopoietic progenitors are present (FIG. 3D). However, CD34 is expressed by a broad range of hematopoietic progenitors that includes lineage committed cells as well as pluripotent progenitors. Therefore, the developmental potential of the ALDH$^{br}$ SSC$^{lo}$ UCB cells was analyzed. Initially, the immunophenotype of these cells was more carefully defined. The immunophenotype would in no way be conclusive; however, the primitiveness of the cell population could be inferred by examining two activation markers that are typically associated with the differentiation of primitive cells to more lineage-committed hematopoietic cells, CD38 and CD71. The most primitive subsets of CD34$^+$ cells have little to no expression of the activation antigens CD38 or CD71. In UCB cell preparations with BAAA and with antibodies specific for CD34 and CD38, the ALDH$^{br}$ SSC$^{lo}$ UCB cells provided a single-step enrichment for essentially purified CD34$^{br}$ CD38$^{dim}$ cells. Furthermore, when CD34$^+$ UCB cells were examined independently, ALDH expression was inversely proportional to the expression of both CD38 and CD71 (FIGS. 4A and 4B). Thus, the ALDH$^{br}$ SSC$^{lo}$ UCB cells appear to contain the primitive CD34$^+$ cells as defined by immunophenotype.

To assay the developmental potential of the ALDH$^{br}$ SSC$^{lo}$ UCB cells, these cells were isolated and placed into both short-term and long-term assays for myeloerythroid progenitors. The short-term assay used, the hematopoietic progenitor colony assay (HPCA), quantifies lineage committed cells at the time of the initial isolation. More primitive progenitors were also assayed by maintaining the ALDH$^{br}$ SSC$^{lo}$ UCB cells on stroma for either 5 or 8 weeks prior to performing the HPCA (FIG. 5).

Results:

HPCA—ALDH$^{br}$ SSC$^{lo}$ essentially equivalent to CD34$^+$ cells.

LTC —5 wk—ALDH$^{br}$ SSC$^{lo}$ essentially equivalent to CD34$^+$ cells.

LTC =8 wk—ALDH$^{br}$ SSC$^{lo}$ outperforms CD34$^+$ cells.

Example 2

ALDH$^{br}$ UCB cells have been shown to be predominantly CD34$^+$CD38$^{-/lo}$ and highly enriched for early myeloid progenitors. The current study was undertaken to determine whether the ALDH$^{br}$ CD34$^+$ UCB cells were enriched for lymphoid progenitors as well. In three experiments, cultures of ALDH$^{br}$ CD34 UCB cells were established on AFT024 stromal cells in the presence of Kit ligand, Flt3 ligand, IL-3 (1st day only), IL-2 and IL-7 at various dilutions. After 7-8 weeks, the cultures were analyzed for lymphocyte growth as determined by expression of CD56, CD10, CD19 or CD20.

TABLE 1

| ALDH$^{br}$ cells/well | total wells initiated | wells with viable cells | lymphocyte$^+$ wells |
|---|---|---|---|
| 1000 | 6 | 5 | 5 |
| 250 | 16 | 12 | 12 |
| 62 | 48 | 40 | 40 |
| 16 | 48 | 34 | 34 |
| 10 | 24 | 20 | 17 |

The AFT024 cultures primarily favored the growth of presumptive NK cells, so to more effectively test whether ALDH$^{br}$ CD34$^+$ UCB cells contained B-lymphoid progenitors, they were cultured on the W20 stromal cell line supplemented with the same cytokine combination. Of 12 cultures established with 100 ALDH$^{br}$ CD34$^+$ cells, all produced CD56$^+$ and CD10$^+$ cells at nearly equivalent proportions. 2 of the 12 wells also contained CD19$^+$ cells.

In summary, the ALDH$^{br}$ CD34$^+$ UCB population appears to be highly enriched for both myeloid and lymphoid hematopoietic progenitors.

All documents cited above are hereby incorporated in their entirety by reference. One skilled in the art will appreciate from a reading of this disclosure that various changes in form and detail can be made without departing from the true scope of the invention.

That which is claimed:

1. A composition consisting essentially of a population of cells having retained therein a detectable product resulting from conversion by the cell of BODIPY aminoacetaldehyde to said detectable product, wherein said detectable product is BODIPY aminoacetate.

2. The composition of claim 1, wherein said population of cells is a human population of cells.

3. The composition of claim 2, wherein said population of cells is from a source selected from the group consisting of umbilical cord blood, bone marrow, peripheral blood and fetal liver.

4. The composition of claim 3, wherein said population of cells is from umbilical cord blood.

5. The composition of claim 3, wherein said population of cells is from bone marrow.

6. The composition of claim 3, wherein said population of cells is from peripheral blood.

7. The composition of claim 3, wherein said population of cells is from fetal liver.

* * * * *